United States Patent
Wewers et al.

(10) Patent No.: US 11,710,560 B2
(45) Date of Patent: Jul. 25, 2023

(54) COMPRESSION OF MACHINE HEALTH DATA

(71) Applicant: epro Gmbh, Gronau (DE)

(72) Inventors: Thomas Wewers, Gronau (DE); Sven Wermers, Gronau (DE)

(73) Assignee: epro Gmbh, Gronau (DE)

(*) Notice: Subject to any disclaimer, the term of this patent is extended or adjusted under 35 U.S.C. 154(b) by 325 days.

(21) Appl. No.: 16/914,647

(22) Filed: Jun. 29, 2020

(65) Prior Publication Data

US 2021/0074418 A1 Mar. 11, 2021

Related U.S. Application Data

(60) Provisional application No. 62/898,772, filed on Sep. 11, 2019.

(51) Int. Cl.
*G16H 40/63* (2018.01)
*G06F 17/18* (2006.01)
*G16H 40/20* (2018.01)

(52) U.S. Cl.
CPC ............ *G16H 40/63* (2018.01); *G06F 17/18* (2013.01); *G16H 40/20* (2018.01)

(58) Field of Classification Search
CPC ........ G16H 40/63; G16H 40/20; G06F 17/18; G06F 16/1744; G06F 16/2462; G06F 16/2474; H03M 7/70; H03M 7/3059; G06Q 10/10; G01D 21/02
USPC ........................................................... 705/2
See application file for complete search history.

(56) References Cited

U.S. PATENT DOCUMENTS

| 4,520,674 A | 6/1985 | Canada et al. |
| 10,248,114 B2* | 4/2019 | Hilemon ............ G06F 16/24578 |
| 10,484,388 B2* | 11/2019 | Hilemon ............... H04L 63/102 |
| 2006/0101111 A1 | 5/2006 | Bouse et al. |

(Continued)

FOREIGN PATENT DOCUMENTS

| DE | 19516481 A1 | 11/1996 |
| DE | 202012003126 U1 | 4/2012 |

(Continued)

OTHER PUBLICATIONS

German Office Action No. P200372DE dated Feb. 22, 2023.

*Primary Examiner* — Garcia Ade
(74) *Attorney, Agent, or Firm* — Luedeka Neely Group PC (57) ABSTRACT

A computer-implemented method reduces an amount of machine health data to be stored in a data storage device while preserving details of extrema values occurring within incremental measurement time intervals in an extended time period during which the data were collected. The method includes: sensing an operational characteristic of a machine and generating an operational characteristic signal; generating machine health parameter data that include amplitude values and associated time values; for each incremental measurement time interval, calculating an average value of the amplitude values, identifying a maximum value of the amplitude values, and identifying a minimum value of the amplitude values; and storing a compressed machine health parameter data set in the data storage device. The compressed machine health parameter data set includes the calculated average values and the identified maximum and minimum values for the incremental measurement time intervals.

18 Claims, 5 Drawing Sheets

(56) References Cited

U.S. PATENT DOCUMENTS

2007/0255851 A1   11/2007  Vrba et al.
2017/0102695 A1*  4/2017  Hilemon ........... G06F 16/24578
2018/0011065 A1*  1/2018  Bowers, III ....... G01N 29/4427

FOREIGN PATENT DOCUMENTS

DE      102017114321 A1    1/2019
WO    WO-2008008919 A2 *  1/2008  ............. G06F 19/18

* cited by examiner

COMPRESSION OF MACHINE HEALTH DATA

RELATED APPLICATIONS

This application claims priority to provisional patent application Ser. No. 62/898,772, titled "Consolidation of Machine Health Data over an Extended Time Period," the entire contents of which are incorporated herein by reference.

FIELD

This invention relates to the field of data storage. More particularly, this invention relates to a system for storing machine health trend data over long time periods, such as years.

BACKGROUND

In some situations involving visualization of machine health trend data, it is desirable to see the trending of values over a long time period, even spanning several years. However, storage of such data over a long time requires a significant amount of memory space.

One solution to the data storage problem is to determine and store only average machine health parameter values over a specific time period (hours, days, month, years). This technique provides sufficient information to indicate that a measured machine health parameter is slowly changing and is beginning to indicate a problem. However, calculating and saving only an average parameter value over a time period results in the loss of extrema of the value. This makes it impossible to see short-term peaks in a plot of average values. Thus, when observing a current level, it is not possible to determine based on historical data whether the current level has been reached before.

What is needed, therefore, is a system for storing average values and the extrema of machine health parameter values.

SUMMARY

The above and other needs are met by a data storage system that determines and saves average values for specific time periods, and also the minimum and maximum values occurring during each time period. Although this requires more memory than is used in storing only the average values, the memory requirements are significantly reduced compared to the original raw data that include all measured values.

One embodiment described herein is directed to a computer-implemented method for reducing an amount of machine health data to be stored in a data storage device while preserving details of extrema values that occur within incremental measurement time intervals within an extended time period during which the machine health data were collected. The method includes:
  (a) sensing an operational characteristic of a machine and generating an operational characteristic signal using a sensor attached to the machine;
  (b) based on the operational characteristic signal, generating machine health parameter data comprising amplitude values and associated time values indicative of the operational characteristic of the machine;
  (c) calculating an average value of the amplitude values occurring within each incremental measurement time interval;
  (d) identifying a maximum value of the amplitude values occurring within each incremental measurement time interval;
  (e) identifying a minimum value of the amplitude values occurring within each incremental measurement time interval; and
  (f) storing a compressed machine health parameter data set in the data storage device, the compressed machine health parameter data set comprising the calculated average values and the identified maximum and minimum values for the incremental measurement time intervals.

In some embodiments, the method includes storing a time value associated with each identified maximum value, and storing a time value associated with the identified minimum value.

In some embodiments, each time value associated with each maximum value indicates a specific time at which a corresponding maximum value in the operational characteristic signal was sensed, and each time value associated with each minimum value indicates a specific time at which a corresponding minimum value in the operational characteristic signal was sensed.

In some embodiments, the compressed machine health parameter data set includes a value indicating a start time of the extended time period, a value indicating an end time of the extended time period, and a value indicating a number of incremental measurement time intervals comprising the extended time period.

In some embodiments, the sensor is a vibration sensor and the operational characteristic signal is a vibration signal.

In some embodiments, the method includes reconstructing the machine health parameter data from the compressed machine health parameter data set for plotting on a display device.

In some embodiments, plotting the machine health parameter data on the display device includes plotting the average values versus time along a first line having a first visual characteristic, plotting the maximum values versus time along a second line having a second visual characteristic that is different from the first visual characteristic, and plotting the minimum values versus time along a third line having a third visual characteristic that is different from the first visual characteristic.

In some embodiments, the second line is an upper boundary of a shaded envelope displayed on the display device, the third line is a lower boundary of the shaded envelope, and the first line is disposed within the shaded envelope.

In another aspect, embodiments described herein are directed to an apparatus for reducing an amount of machine health data to be stored in a data storage device while preserving details of extrema values that occur during incremental measurement time intervals within an extended time period during which the machine health data were collected. The apparatus includes a sensor, a machine health monitoring device, one or more processors, and a storage device. The sensor senses an operational characteristic of a machine and generates an operational characteristic signal. The machine health monitoring device receives the operational characteristic signal and generates machine health parameter data based thereon. The machine health parameter data include amplitude values and associated time values indicative of the operational characteristic of the machine. The one or more processors generate a compressed machine health parameter data set. This involves, for each incremental measurement time interval, calculating an average value of the amplitude values occurring within the incremental measurement time interval, identifying a maximum value of the amplitude values occurring within the incremental measurement time interval, and identifying a minimum value of the amplitude values occurring within the incremental measurement time interval. The storage device stores the compressed machine health parameter data set.

In some embodiments, the compressed machine health parameter data set includes a time value associated with each identified maximum value and a time value associated with each identified minimum value.

In some embodiments, each time value associated with each maximum value indicates a specific time at which a corresponding maximum value in the operational characteristic signal was sensed, and each time value associated with each minimum value indicates a specific time at which a corresponding minimum value in the operational characteristic signal was sensed.

In some embodiments, the compressed machine health parameter data set includes a value indicating a start time of the extended time period, a value indicating an end time of the extended time period, and a value indicating a number of incremental measurement time intervals comprising the extended time period.

In some embodiments, the sensor comprises a vibration sensor and the operational characteristic signal comprises a vibration signal.

In some embodiments, the apparatus includes a display device, and the one or more processors reconstruct the machine health parameter data from the compressed machine health parameter data set for plotting on the display device.

In some embodiments, the machine health parameter data plotted on the display device include average values versus time plotted along a first line having a first visual characteristic, the maximum values versus time plotted along a second line having a second visual characteristic that is different from the first visual characteristic, and the minimum values versus time plotted along a third line having a third visual characteristic that is different from the first visual characteristic.

In some embodiments, the second line comprises an upper boundary of a shaded envelope displayed on the display device, the third line comprises a lower boundary of the shaded envelope, and the first line is disposed within the shaded envelope.

In some embodiments, at least one of the one or more processors is a component of the machine health monitoring device, or a portable machine health analyzer, or a continuous online machine health monitoring system.

In some embodiments, at least one of the one or more processors is a component of a server computer that is in communication with the portable machine health analyzer or the continuous online machine health monitoring system.

In yet another aspect, embodiments described herein are directed to a computer-implemented method for processing and displaying machine health data that were collected during incremental measurement time intervals over an extended time period. In on preferred embodiment, the method includes:

(a) sensing vibration of a machine and generating a vibration signal using a vibration sensor attached to the machine;
(b) generating machine health parameter data based on the vibration signal, the machine health parameter data comprising amplitude values and associated time values indicative of an operational characteristic of the machine;
(c) for each incremental measurement time interval:
   calculating an average value of the amplitude values occurring within the incremental measurement time interval;
   identifying a maximum value of the amplitude values occurring within the incremental measurement time interval; and
   identifying a minimum value of the amplitude values occurring within the incremental measurement time interval;
(d) storing a compressed machine health parameter data set in the data storage device, the compressed machine health parameter data set comprising:
   the average values;
   the maximum values;
   the minimum values;
   time values associated with the maximum values, each indicating a specific time at which a corresponding maximum value in the vibration signal was sensed in step (a); and
   time values associated with the minimum values, each indicating a specific time at which a corresponding minimum value in the vibration signal was sensed in step (a);
(e) reconstructing the machine health parameter data from the compressed machine health parameter data set for plotting on a display device; and
(f) plotting the machine health parameter data on a display device, comprising:
   plotting the average values versus time along a first line having a first visual characteristic;
   plotting the maximum values versus time along a second line having a second visual characteristic that is different from the first visual characteristic; and
   plotting the minimum values versus time along a third line having a third visual characteristic that is different from the first visual characteristic.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
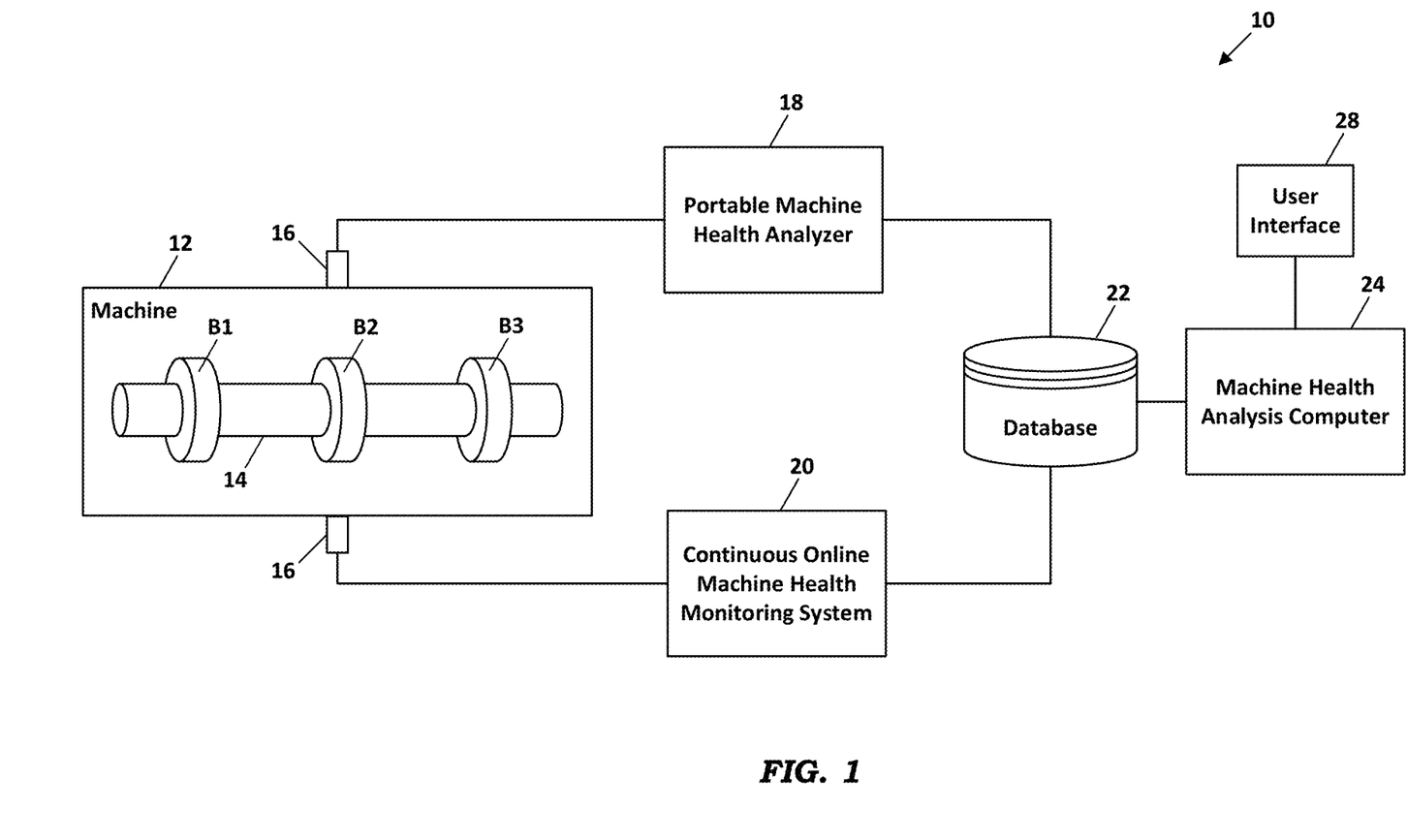
FIG. 1 depicts a machine health data collection and analysis system according to an embodiment of the invention.
Figure 2:
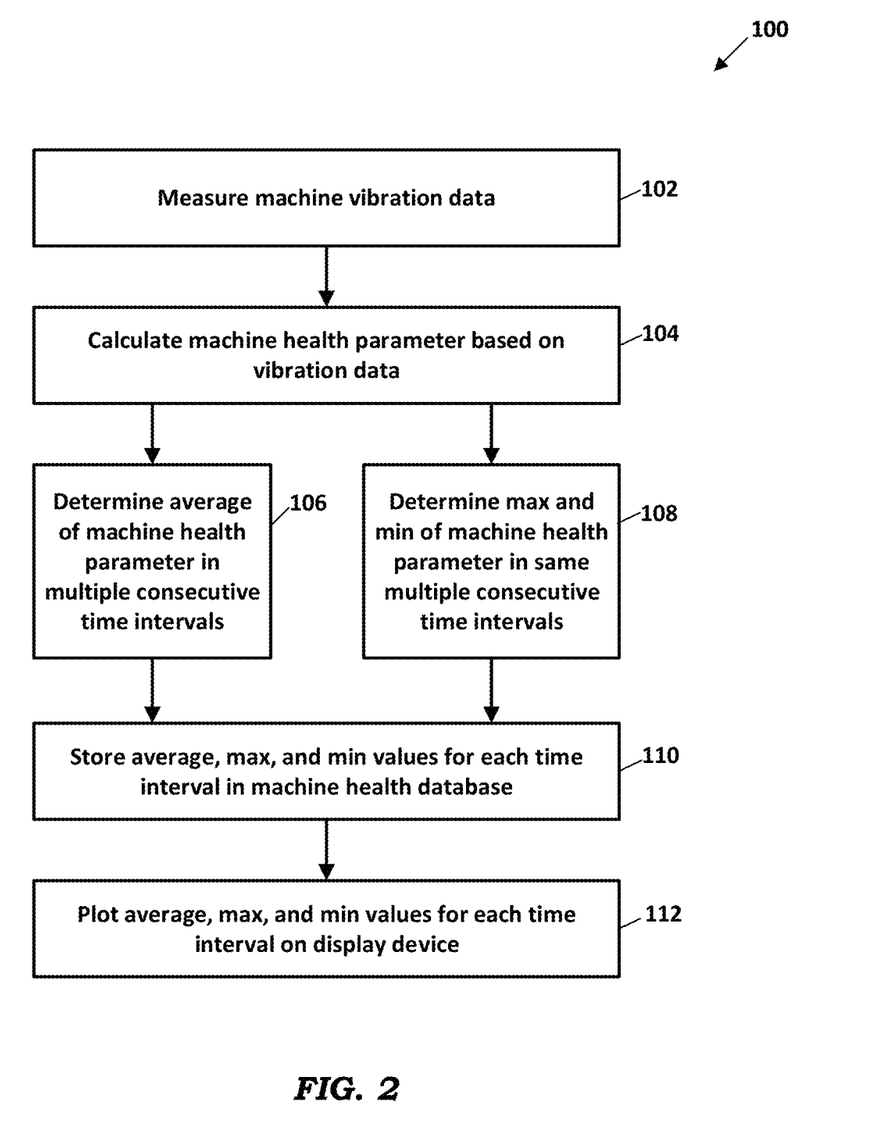
FIG. 2 depicts a method for processing and displaying machine health data according to an embodiment of the invention.

FIG. 1 depicts a machine health measurement and analysis system 10 that includes sensors, such as vibration sensors 16, attached to a machine 12. In other embodiments, parameters indicative of machine health other than vibration may be sensed, such as current or flux. FIG. 2 depicts a process 100 performed using the system 10 of FIG. 1 to collect, compress and analyze machine health data, and display the data in a graphical plot that allows an operator to easily ascertain the overall health of the machine 12.

As shown in FIG. 1, the machine 12 may include at least one rotating component 14, such as a shaft supported by bearings B1, B2, and B3. The vibration sensors 16 generate vibration signals indicative of the vibration of the machine 12, which include vibration components associated with the bearings B1, B2, and B3. In a preferred embodiment, the vibration signals are received, conditioned, and converted to time waveform digital data by one or more machine health data collectors, such as a portable machine health analyzer 18 or a continuous online machine health monitoring system 20 (step 102 in FIG. 2). The machine health data collectors 18 and 20 include signal conditioning circuitry and analog-to-digital conversion circuitry for conditioning the vibration signals from the sensors 16 and generating the time waveform digital vibration data based thereon. In various embodiments, a processor in the portable machine health analyzer 18, or in the continuous online machine health monitoring system 20, or in the machine health analysis computer 24 performs steps 104 through 110 in the method of FIG. 2.

Based on the measured vibration data, one or more machine health parameters are calculated (step 104). In general, a machine health parameter is any scalar value or other type of value that may be trended to indicate the general health of a machine over time. Examples of such machine health parameters include: results from health calculation rules for mechanical faults, electrical issues, looseness, cavitation, balance, air gap, lubrication, alignment, blade pass, and stall; fuzzy rules with multiple inputs or values like Overall Vibration; amplitude of characteristic frequency bands; temperature; PeakVue values; PeakVue Plus values; ratio of power between harmonic and nonharmonic parts in the vibration; and other health indicating values.

In a preferred embodiment, the machine health parameter data collected over an extended period of time are broken into multiple consecutive time intervals. For example, each time interval may be five seconds in duration. The data may comprise a machine health parameter value calculated at one-second increments based on the collected vibration data. This results in five machine health parameter values calculated per time interval. An average of the five machine health parameter values is determined for each time interval (step 106), as are the maximum and minimum of the five machine health parameter values (step 108). This compression technique results in three data values stored for each consecutive time interval instead of five data values (step 110).

The compressed vibration time waveform data are preferably downloaded to a machine health database 22 for long term storage. The data in the database 22 are available for analysis by software routines executed on a machine health analysis computer 24. Alternatively, the vibration time waveform data are stored in data storage devices in the portable machine health analyzer 18 or the continuous online machine health monitoring system 20. In preferred embodiments, the system 10 includes a user interface 28, such as a computer monitor or touch screen, that allows a user to view measurement results, select certain measurement parameters, and provide other input as described herein.

Figure 3A:
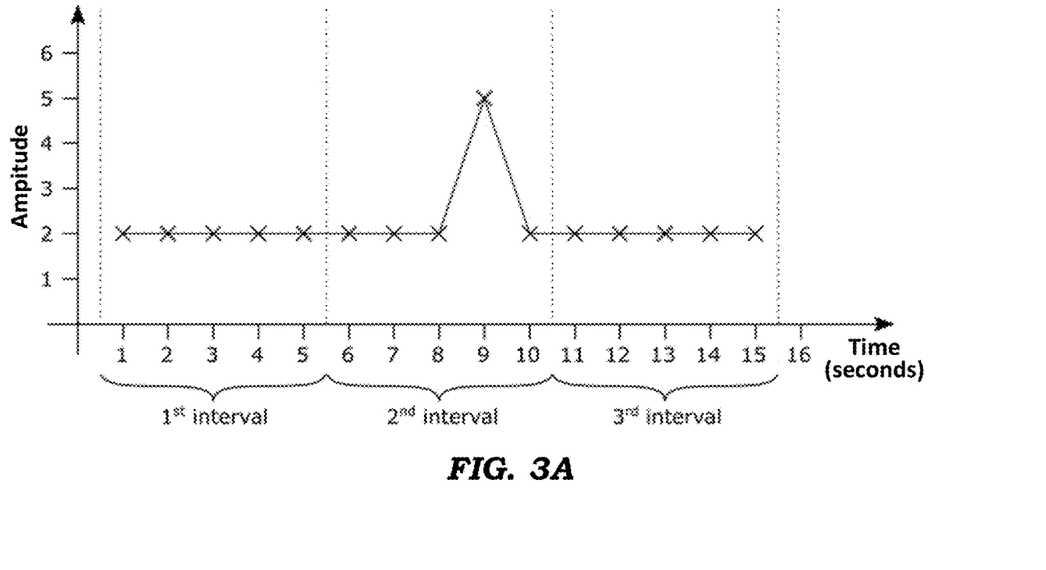
FIGS. 3A and 3B are graphical depictions of average and extrema values of machine health data collected during three consecutive five-second time intervals according to an embodiment of the invention.
Figure 3B:
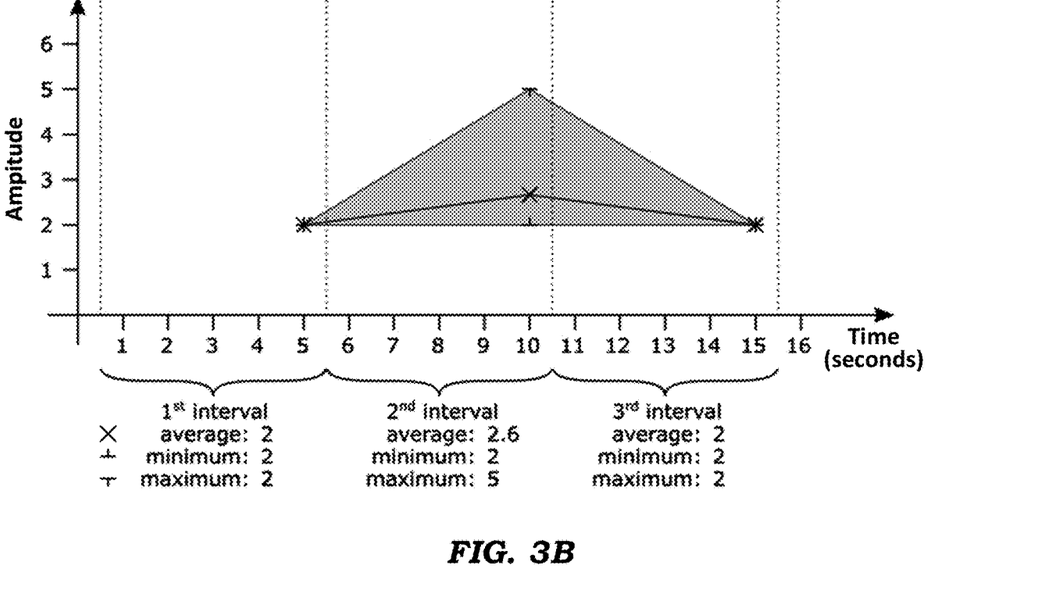

As depicted in FIG. 3B, visualizing the data is possible by plotting the average value for each time interval (designated by x) in combination with the minimum (⊥) and maximum (⊤) values in the time interval (step 112 in FIG. 2). This allows the user to visualize not only the minimum and maximum values, but also how much these values are deviating from the average value. As in the example described above, the raw data (depicted in FIG. 3A) may include five data points in each of the three five-second time intervals, whereas the compressed data set for each interval includes only three data points: the maximum, the minimum, and the average. For this example, storing only the average, maximum, and minimum values results in a compression ratio of $(1-3/5) \times 100\% = 40\%$.

In a preferred embodiment, the time values corresponding to the maximum and minimum values for each interval are also stored. In some cases, these time values may help an analyst better understand why a maximum or minimum value significantly differs from the average value. For example, a particular identifiable event may have occurred at a time that corresponds to the time of the maximum or minimum extreme.

Figure 4:
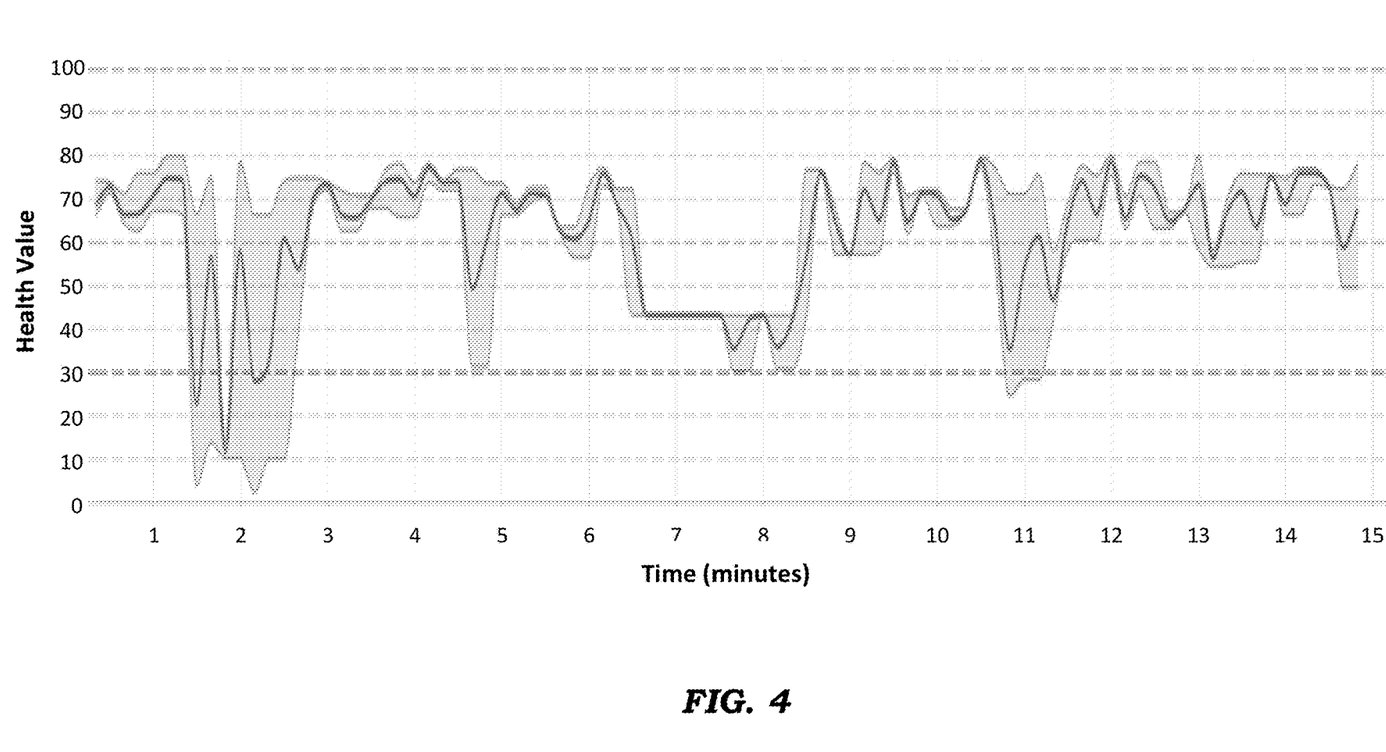
FIG. 4 is a graphical depiction of average and extrema values of machine health data collected during a fifteen-minute time period according to an embodiment of the invention.

FIG. 4 depicts an exemplary plot of compressed overall asset health trend data over a 15 minute time interval. The running average value is depicted as the bold line, and the maximum and minimum values are represented as the upper and lower boundaries of the shaded envelope.

Figure 5:
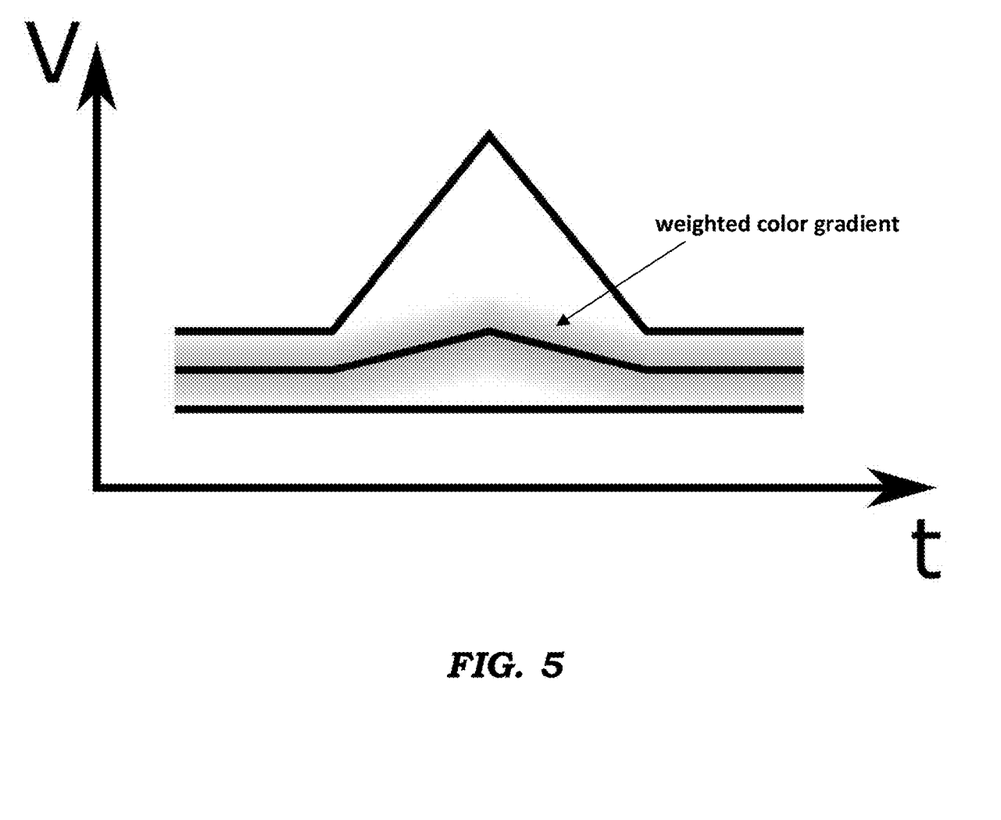
FIG. 5 is a graphical depiction of average and extrema values of machine health data including a weighted color gradient to animate how many values contribute to each plotted level of minimum and maximum.

FIG. 5 depicts an exemplary plot generated by an embodiment in which the graphical display includes a weighted color gradient to animate how many values contribute to each plotted level of minimum and maximum.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A computer-implemented method for reducing an amount of machine health data to be stored in a data storage device while preserving details of extrema values that occur within incremental measurement time intervals in an extended time period during which the machine health data were collected, the method comprising:
   (a) sensing an operational characteristic of a machine and generating an operational characteristic signal using a sensor attached to the machine;
   (b) a computer processor generating machine health parameter data based on the operational characteristic signal, the machine health parameter data comprising amplitude values and associated time values indicative of the operational characteristic of the machine, wherein the amplitude values and associated time values occur during the incremental measurement time intervals within the extended time period;
   (c) for each incremental measurement time interval, the computer processor calculating a single average value of all of the amplitude values occurring within the incremental measurement time interval;

(d) for each incremental measurement time interval, the computer processor identifying a maximum value of the amplitude values occurring within the incremental measurement time interval;

(e) for each incremental measurement time interval, the computer processor identifying a minimum value of the amplitude values occurring within the incremental measurement time interval; and (f) storing a compressed machine health parameter data set in the data storage device, the compressed machine health parameter data set comprising the calculated average values and the identified maximum and minimum values for the incremental measurement time intervals, wherein the compressed machine health parameter data set preserves details of extrema values that occur within the incremental measurement time intervals while requiring less data storage capacity than would be required to store the machine health parameter data from which the compressed machine health parameter data set was derived.

2. The method of claim 1 further comprising:
for each maximum value identified in step (d), storing a time value associated with the maximum value; and
for each minimum value identified in step (e), storing a time value associated with the minimum value.

3. The method of claim 2 wherein each time value associated with each maximum value indicates a specific time at which a corresponding maximum value in the operational characteristic signal was sensed in step (a), and each time value associated with each minimum value indicates a specific time at which a corresponding minimum value in the operational characteristic signal was sensed in step (a).

4. The method of claim 1 wherein step (f) further comprises storing the compressed machine health parameter data set including a value indicating a start time of the extended time period, a value indicating an end time of the extended time period, and a value indicating a number of incremental measurement time intervals comprising the extended time period.

5. The method of claim 1 wherein the sensor comprises a vibration sensor and the operational characteristic signal comprises a vibration signal.

6. The method of claim 1 further comprising reconstructing the machine health parameter data from the compressed machine health parameter data set for plotting on a display device.

7. The method of claim 6 wherein plotting the machine health parameter data on the display device comprises plotting the average values versus time along a first line having a first visual characteristic, plotting the maximum values versus time along a second line having a second visual characteristic that is different from the first visual characteristic, and plotting the minimum values versus time along a third line having a third visual characteristic that is different from the first visual characteristic.

8. The method of claim 7 wherein the second line comprises an upper boundary of a shaded envelope displayed on the display device, the third line comprises a lower boundary of the shaded envelope, and the first line is disposed within the shaded envelope.

9. An apparatus for reducing an amount of machine health data to be stored in a data storage device while preserving details of extrema values that occur during incremental measurement time intervals in an extended time period during which the machine health data were collected, the apparatus comprising:

a sensor for sensing an operational characteristic of a machine and generating an operational characteristic signal;

a machine health monitoring device that receives the operational characteristic signal and generates machine health parameter data based thereon, the machine health parameter data comprising amplitude values and associated time values indicative of the operational characteristic of the machine;

one or more processors that generate a compressed machine health parameter data set by, for each incremental measurement time interval:
calculating a single average value of all of the amplitude values occurring within the incremental measurement time interval;
identifying a maximum value of the amplitude values occurring within the incremental measurement time interval; and
identifying a minimum value of the amplitude values occurring within the incremental measurement time interval; and a storage device that stores the compressed machine health parameter data set, wherein the compressed machine health parameter data set preserves details of extrema values that occur within the incremental measurement time intervals while requiring less data storage capacity than would be required to store the machine health parameter data from which the compressed machine health parameter data set was derived.

10. The apparatus of claim 9 wherein the one or more processors generate the compressed machine health parameter data set to include a time value associated with each identified maximum value and a time value associated with each identified minimum value.

11. The apparatus of claim 10 wherein each time value associated with each maximum value indicates a specific time at which a corresponding maximum value in the operational characteristic signal was sensed, and each time value associated with each minimum value indicates a specific time at which a corresponding minimum value in the operational characteristic signal was sensed.

12. The apparatus of claim 9 wherein the one or more processors generate the compressed machine health parameter data set to include a value indicating a start time of the extended time period, a value indicating an end time of the extended time period, and a value indicating a number of incremental measurement time intervals comprising the extended time period.

13. The apparatus of claim 9 wherein the sensor comprises a vibration sensor and the operational characteristic signal comprises a vibration signal.

14. The apparatus of claim 9 further comprising a display device, wherein the one or more processors reconstruct the machine health parameter data from the compressed machine health parameter data set for plotting on the display device.

15. The apparatus of claim 14 wherein the machine health parameter data plotted on the display device include average values versus time plotted along a first line having a first visual characteristic, the maximum values versus time plotted along a second line having a second visual characteristic that is different from the first visual characteristic, and the minimum values versus time plotted along a third line having a third visual characteristic that is different from the first visual characteristic.

16. The apparatus of claim 15 wherein the second line comprises an upper boundary of a shaded envelope displayed on the display device, the third line comprises a lower boundary of the shaded envelope, and the first line is disposed within the shaded envelope.

17. The apparatus of claim 9 wherein at least one of the one or more processors is a component of the machine health monitoring device, or a portable machine health analyzer, or a continuous online machine health monitoring system.

18. The apparatus of claim 17 wherein at least one of the one or more processors is a component of a server computer that is in communication with the machine health monitoring device, the portable machine health analyzer, or the continuous online machine health monitoring system.

* * * * *